(12) United States Patent
Lewis et al.

(10) Patent No.: US 7,601,336 B2
(45) Date of Patent: *Oct. 13, 2009

(54) PHARMACEUTICAL AEROSOL COMPOSITION

(75) Inventors: David Lewis, Parma (IT); Davis Ganderton, Parma (IT); Brian Meakin, Parma (IT); Paolo Ventura, Parma (IT); Gaetano Brambilla, Parma (IT); Raffaella Garzia, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 649 days.

This patent is subject to a terminal disclaimer.

(21) Appl. No.: 10/435,032

(22) Filed: May 12, 2003

(65) Prior Publication Data

US 2003/0206870 A1   Nov. 6, 2003

Related U.S. Application Data

(63) Continuation of application No. 09/796,607, filed on Mar. 2, 2001, now abandoned, which is a continuation of application No. 09/147,669, filed as application No. PCT/EP98/03533 on Jun. 10, 1998, now abandoned.

(30) Foreign Application Priority Data

Jun. 13, 1997   (GB) .................................. 9712434.1

(51) Int. Cl.
*A61K 9/12* (2006.01)
*A61K 9/14* (2006.01)
*A61K 9/00* (2006.01)

(52) U.S. Cl. ............................. 424/43; 424/44; 424/45; 424/46; 424/47; 514/958

(58) Field of Classification Search ............. 424/43–47; 514/958
See application file for complete search history.

(56) References Cited

U.S. PATENT DOCUMENTS

| | | |
|---|---|---|
| 3,361,306 A | 1/1968 | Grim |
| 3,622,053 A | 11/1971 | Ryden |
| 4,185,100 A | 1/1980 | Rovee et al. |
| 4,425,339 A | 1/1984 | Pitchford |
| 4,499,108 A | 2/1985 | Sequeira et al. |
| 4,579,854 A | 4/1986 | Iwakuma et al. |
| 4,584,320 A | 4/1986 | Rubin et al. |
| 4,621,077 A | 11/1986 | Rosini et al. |
| 4,761,406 A | 8/1988 | Flora et al. |
| 4,812,304 A | 3/1989 | Anderson et al. |
| 4,812,311 A | 3/1989 | Uchtman |
| 4,822,609 A | 4/1989 | Flora |
| 4,835,145 A | 5/1989 | MacDonald |
| 4,927,814 A | 5/1990 | Gall et al. |
| 4,980,171 A | 12/1990 | Fels et al. |
| 5,192,528 A | 3/1993 | Radhakrishnan et al. |
| 5,227,506 A | 7/1993 | Saari et al. |
| 5,248,493 A | 9/1993 | Brown |
| 5,270,365 A | 12/1993 | Gertz et al. |
| 5,358,941 A | 10/1994 | Bechard et al. |
| 5,366,965 A | 11/1994 | Strein |
| 5,415,853 A * | 5/1995 | Hettche et al. ................. 424/45 |
| 5,435,297 A | 7/1995 | Klein |
| 5,488,041 A | 1/1996 | Barbier et al. |
| 5,502,076 A * | 3/1996 | Dixit et al. ................... 514/510 |
| 5,583,122 A | 12/1996 | Benedict et al. |
| 5,605,674 A | 2/1997 | Purewal |
| 5,616,560 A | 4/1997 | Geddes |
| 5,616,571 A | 4/1997 | Daifotis et al. |
| 5,622,721 A | 4/1997 | Dansereau et al. |
| 5,642,728 A | 7/1997 | Andersson et al. |
| 5,653,961 A | 8/1997 | McNally et al. |
| 5,676,930 A * | 10/1997 | Jager et al. ..................... 424/45 |
| 5,683,677 A | 11/1997 | Purewal et al. |
| 5,695,743 A | 12/1997 | Purewal et al. |
| 5,773,429 A | 6/1998 | Fuisz |
| 5,776,433 A | 7/1998 | Tzou et al. |
| 5,780,455 A | 7/1998 | Brenner et al. |
| 5,804,570 A | 9/1998 | Santora, II et al. |
| 5,853,759 A | 12/1998 | Katdare et al. |
| 5,891,419 A | 4/1999 | Cutie |

(Continued)

FOREIGN PATENT DOCUMENTS

EP   0128 736   A1   12/1984

(Continued)

OTHER PUBLICATIONS

Handbook of Pharmaceutical Excipients, $3^{rd}$ Ed., pp. 7-9, 220-222, 234-235, 560-561.
Harrison et al, *J. Pharm. Pharmacol.*, 1996, vol. 48, pp. 596-600.
Hoet et al, *The Lancet*, 1997, vol. 350, pp. 556-559.
Daly, Jr., *Aerosol Age*, Feb. 1990, pp. 26, 27, 40 and 57.
Strobach, *Aerosol Age*, Jul. 1988, pp. 32, 33, 42 and 43.
Tzou et al, *Journal of Pharmaceutical Sciences*, 1997, vol. 86, No. 12, pp. 1352-1357.
Kontny et al, *Journal of Aerosol Medicine*, 1991, vol. 4, No. 3, pp. 181-187.

(Continued)

*Primary Examiner*—Sreeni Padmanabhan
*Assistant Examiner*—Renee Claytor
(74) *Attorney, Agent, or Firm*—Oblon, Spivak, McClelland, Maier & Neustadt, L.L.P.

(57) ABSTRACT

A composition for use in an aerosol inhaler, the composition comprising an active material, a propellant containing a hydrofluoroalkane (HFA), a cosolvent and further comprising a low volatility component to increase the mass median aerodynamic diameter (MMAD) of the aerosol particles on actuation of the inhaler, filling of an aerosol container and use of the composition for the administration of active materials by inhalation.

8 Claims, No Drawings

U.S. PATENT DOCUMENTS

| | | | |
|---|---|---|---|
| 5,954,047 A | 9/1999 | Armer et al. | |
| 5,955,058 A | 9/1999 | Jager et al. | |
| 5,994,329 A | 11/1999 | Daifotis et al. | |
| 6,004,537 A | 12/1999 | Blondino et al. | |
| 6,006,745 A | 12/1999 | Marecki | |
| 6,026,808 A | 2/2000 | Armer et al. | |
| 6,045,778 A | 4/2000 | Jager et al. | |
| 6,045,784 A | 4/2000 | Ruebusch et al. | |
| 6,131,566 A | 10/2000 | Ashurst | |
| 6,143,277 A | 11/2000 | Ashurst et al. | |
| 6,149,892 A * | 11/2000 | Britto | 424/45 |
| 6,150,418 A | 11/2000 | Hochrainer et al. | |
| 6,225,294 B1 | 5/2001 | Daifotis et al. | |
| 6,241,969 B1 | 6/2001 | Saidi et al. | |
| 6,253,762 B1 | 7/2001 | Britto | |
| 6,290,930 B1 | 9/2001 | Blondino et al. | |
| 6,315,985 B1 | 11/2001 | Wu et al. | |
| 6,413,496 B1 | 7/2002 | Goodman et al. | |
| 6,432,932 B1 | 8/2002 | Daifotis et al. | |
| 6,451,285 B2 | 9/2002 | Blondino et al. | |
| 6,645,466 B1 | 11/2003 | Keller et al. | |
| 6,713,047 B1 | 3/2004 | Lewis et al. | |
| 6,716,414 B2 | 4/2004 | Lewis et al. | |
| 6,964,759 B2 * | 11/2005 | Lewis et al. | 424/45 |
| 7,018,618 B2 | 3/2006 | Lewis et al. | |
| 2001/0031244 A1 | 10/2001 | Lewis et al. | |
| 2003/0066525 A1 | 4/2003 | Lewis et al. | |
| 2003/0077230 A1 | 4/2003 | Blondino et al. | |
| 2003/0089369 A1* | 5/2003 | Lewis et al. | 128/200.23 |
| 2003/0157028 A1 | 8/2003 | Lewis et al. | |
| 2003/0190287 A1 | 10/2003 | Lewis et al. | |
| 2003/0190289 A1* | 10/2003 | Lewis et al. | 424/45 |
| 2003/0206870 A1 | 11/2003 | Lewis et al. | |
| 2004/0047809 A1 | 3/2004 | Lewis et al. | |
| 2004/0062720 A1* | 4/2004 | Lewis et al. | 424/46 |
| 2004/0096399 A1* | 5/2004 | Lewis et al. | 424/45 |
| 2004/0184993 A1* | 9/2004 | Lewis et al. | 424/45 |
| 2005/0034720 A1* | 2/2005 | Brambilla et al. | 128/200.23 |
| 2005/0061314 A1* | 3/2005 | Davies et al. | 128/200.23 |
| 2005/0129621 A1* | 6/2005 | Davies et al. | 424/45 |
| 2005/0142071 A1 | 6/2005 | Lewis et al. | |
| 2005/0152846 A1 | 7/2005 | Davies et al. | |
| 2006/0083693 A1 | 4/2006 | Lewis et al. | |
| 2006/0120966 A1 | 6/2006 | Church et al. | |

FOREIGN PATENT DOCUMENTS

| | | |
|---|---|---|
| EP | 0 504 112 A2 | 9/1992 |
| EP | 0 372 777 B1 | 1/1993 |
| EP | 0 642 992 A2 | 3/1995 |
| EP | 0 653 204 | 5/1995 |
| EP | 0 911 048 | 4/1999 |
| EP | 1 157 689 | 11/2001 |
| GB | 1 525 181 | 9/1978 |
| GB | 2 326 334 | 12/1998 |
| HU | P9403762 | 9/1995 |
| HU | P9602888 | 3/1997 |
| WO | WO 91/11173 | 8/1991 |
| WO | WO 9206675 A1 * | 4/1992 |
| WO | WO 92/11236 | 7/1992 |
| WO | WO 92/20391 | 11/1992 |
| WO | WO 93/05765 | 4/1993 |
| WO | WO 93/11743 | 6/1993 |
| WO | WO 93/11747 | 6/1993 |
| WO | WO 93/18746 | 9/1993 |
| WO | WO 94/13262 | 6/1994 |
| WO | WO 94/14490 | 7/1994 |
| WO | WO 94/21228 | 9/1994 |
| WO | WO 94/21229 | 9/1994 |
| WO | WO 95/17195 | 6/1995 |
| WO | WO 96/18384 | 6/1996 |
| WO | WO 96/19198 | 6/1996 |
| WO | WO 96/19968 | 7/1996 |
| WO | WO 96/19969 | 7/1996 |
| WO | WO 96/32099 | 10/1996 |
| WO | WO 96/32150 | 10/1996 |
| WO | WO 96/32151 | 10/1996 |
| WO | WO 96/32345 | 10/1996 |
| WO | WO 96/38156 | 12/1996 |
| WO | WO 97/47286 | 12/1997 |
| WO | WO 98/01147 | 1/1998 |
| WO | WO 98/03533 | 1/1998 |
| WO | WO 98/05302 | 2/1998 |
| WO | WO 98/13031 | 4/1998 |
| WO | WO 98/24420 | 6/1998 |
| WO | WO 98/34595 | 8/1998 |
| WO | WO 98/34596 | 8/1998 |
| WO | WO 98/56349 | 12/1998 |
| WO | WO 99/12596 | 3/1999 |
| WO | WO 99/64014 | 12/1999 |
| WO | WO 99/65460 | 12/1999 |
| WO | WO 99/65464 | 12/1999 |
| WO | WO 00/06121 | 2/2000 |
| WO | WO 00/07567 | 2/2000 |
| WO | WO 00/23065 | 4/2000 |
| WO | WO 00/30608 | 6/2000 |
| WO | WO 00/35458 | 6/2000 |
| WO | WO 00/53157 | 9/2000 |
| WO | WO 00/78286 | 12/2000 |
| WO | WO 01/47493 | 7/2001 |
| WO | WO 01/89480 | 11/2001 |
| WO | WO 03/074023 | 9/2003 |

OTHER PUBLICATIONS

Tansey, *The Pharmaceutical Journal*, 1997, vol. 259, pp. 896-898.

Tiwari et al, *Drug Development and Industrial Pharmacy*, 1998, vol. 24, No. 4, pp. 345-352.

Hankbook of Pharmaceutical Excipients, 3$^{rd}$ Ed., Kibbe Editor, pp. 7-9, 220-222, 234-235, 560, 561.

Men's Osteoporosis Support Group, vol. 1, Issue 2, Jul. 1, 1997.

Rote List 1997, 66 023 (Fosamax).

Reddy M.S. et al, J. Periodontol, 1995, vol. 66(3), pp. 211-217, "Alendronate Treatment of Naturally-Occurring Periodontitis in Beagle Dogs".

Fleisch H., "Bisphosphonates in Bone Disesase from the Laboratory to the patient", 1995 (Book).

Affidavit of Gideon Rodan from validity trial of IL 94612 dated Nov. 17, 2000.

Merck & Co., Inc.—Instructions for Once Weekly Fosamax, Jan. 2001.

Lombardi et al., Ann. Ital. Med. Int. 7, 1992, 3 Suppl., pp. 158-165, "Clinical trials with bisphosphonates".

Reid et al, American Journal of Medicine, 1996, vol. 101, pp. 341-348, "Biochemical and Radiologic Improvement in Paget's Disease of Bone Treated with Alendronate: A Randomized, Placebo-controlled Trial".

Passeri et al, Bone and Mineral, 1991, vol. 15, pp. 237-248, "Intermittent treatment with intravenous 4-amino-1-hydroxybutylidene-1,1-bisphosphonate (AHBuBP) in the therapy of postmenopausal osteoporosis".

Devogelaer et al, Bone, 1996, vol. 18(2), pp. 141-150, "Oral Alendronate Induces Progressive Increases in Bone Mass of the Spine, Hip, and Total Body Over 3 Years in Postmenopausal Women with Osteoporosis".

Siris et al, J. Clin. Endo. Metab., 1996, vol. 81(3), pp. 961-967, "Comparative Study of Alendronate Versus Etidronate for the Treatment of Paget's Disease of Bone".

Toolan et al, J. Bone Min. Res., 1992, vol. 3, pp. 1399-1406, "Effects of 4-Amino-1-Hydroxybutylidene Bisphosphonate on Bone Biomechanics in Rats".

Fleisch et al, Hormone and Metabolic Research, vol. 29 (1997), pp. 145-150, "Bisphosphonates: Mechanisms of Action and Clinical Use in Osteoporosis—An Update".

E-mail communication of Feb. 20, 1998 from Melton to DiCesare et al.
U.S. Appl. No. 10/435,032, filed May 12, 2003, Lewis, et al.
U.S. Appl. No. 10/612,067, filed Jul. 3, 2003, Lewis, et al.
U.S. Appl. No. 10/612,072, filed Jul. 3, 2003, Lewis, et al.
U.S. Appl. No. 10/640,005, filed Aug. 14, 2003, Lewis, et al.
U.S. Appl. No. 10/766,857, filed Jan. 30, 2004, Lewis, et al.
U.S. Appl. No. 11/060,564, filed Feb. 18, 2005, Lewis, et al.
U.S. Appl. No. 11/408,026, filed Apr. 21, 2006, Lewis, et al.
U.S. Appl. No. 09/831,888, filed Jul. 19, 2001, Lewis, et al.
U.S. Appl. No. 09/147,669, filed Feb. 24, 1999, Lewis, et al.
R.O. Williams III et al, "A study of an epoxy aerosol can lining exposed to hydrofluoroalkane propellants", *European Journal of Pharmaceutics and Biopharmaceutics*, vol. 44, pp. 195-203, (1997).
*ABPI Compendium of Data Sheets and Summaries of Product Characteristics*, Datapharm Publications Limited, London, pp. 81-82, (1996-97).
Paul A. Sanders, Ph.D., "Homogeneous Systems and Their Properties", *Handbook of Aerosol Technology*, Second Edition, Van Nostrand Reinhold Company, NY, p. 30, 1979.
G. Brambilla et al, "Modulation of Aerosol Clouds Produced by HFA Solution Inhalers", *Portable Inhalers*, pp. 155-159, (Nov. 26 & 27, 1998).

B. Meakin, "Fine Particle Dose Control of Solution Based pMDIs", *Drug Delivery to the Lungs IX*, The Aerosol Society, pp. 1-20, (Dec. 14 & 15, 1998).
S.S. Davis, "Physico-Chemical Studies on Aerosol Solutions For Drug Delievery I. Water-Propylene Glycol Systems", *International Journal of Pharmaceutics*, 1, 1978, pp. 71-83.
L. I. Harrison et al, "Pharmacokinetics and Dose Proportionality of Beclomethasone From Three Strengths of A CFC-Free Beclomethasone Dipropionate Metered-Dose Inhaler", *Biopharmaceutics & Drug Disposition*, 1997, vol. 18, No. 7, pp. 635-643.
Chet Leach, "Enhanced Drug Delivery Through Reformulating MDIs with HFA Propellants-Drug Deposition and Its Effect on Preclinical and Clinical Programs", *Respiratory Drug Delivery V*, 1996, pp. 133-144.
G. Brambilla et al, "Modulation of Aerosol Clouds Produced By HFA Solution Inhalers", *Drug Delivery to The Lungs*, Dec. 14-15, 1998, The Aerosol Society, pp. 155-159.
*Hackh's Chemical Dictionary*, $4^{th}$ ed., McGraw-Hill, New York, pp. 624 and 650, 1969.

* cited by examiner

PHARMACEUTICAL AEROSOL COMPOSITION

CROSS REFERENCES TO RELATED APPLICATIONS

This application is a continuation of U.S. patent application Ser. No. 09/796,607, filed Mar. 2, 2001, now abandoned, which was a continuation of U.S. patent application Ser. No. 09/147,669, filed Feb. 24, 1999, now abandoned, which was a 371 of International Patent Application No. PCT/EP98/03533, filed on Jun. 10, 1998, and claims priority to UK Application No. 9712434.1, filed on Jun. 13, 1997.

BACKGROUND OF THE INVENTION

1. Field of the Invention

The invention relates to aerosol compositions for pharmaceutical use. In particular, this invention relates to aerosol compositions for use in pressurised metered dose inhalers (MDI). The invention also relates to the use of certain components in aerosol compositions, a method for their preparation and to their use for the administration of active material by inhalation.

2 Description of the Background

Inhalers are well known devices for administering pharmaceutical products to the respiratory tract by inhalation.

Active materials commonly delivered by inhalation include bronchodilators such as β2 agonists and anticholinergics, corticosteroids, anti-leukotrienes, anti-allergics and other materials that may be efficiently administered by inhalation, thus increasing the therapeutic index and reducing side effects of the active material.

There are a number of types of inhaler currently available. The most widely used type is a pressurised metered dose inhaler (MDI) which uses a propellant to expel droplets containing the pharmaceutical product to the respiratory tract as an aerosol. Formulations used in MDIs (aerosol formulations) generally comprise the active material, one or more liquefied propellants and a surfactant or a solvent.

For many years the preferred propellants used in aerosols for pharmaceutical use have been a group of chlorofluorocarbons which are commonly called Freons or CFCs, such as $CCl_3F$ (Freon 11 or CFC-11), $CCl_2F_2$ (Freon 12 or CFC-12), and $CClF_2$-$CClF_2$ (Freon 114 or CFC-114). Chlorofluorocarbons have properties particularly suitable for use in aerosols, including high vapour pressure which generates clouds of droplets of a suitable particle size from the inhaler.

Recently, the chlorofluorocarbon (CFC) propellants such as Freon 11 and Freon 12 have been implicated in the destruction of the ozone layer and their production is being phased out.

In 1987, under the auspices of the United Nations Environmental Programme, the Montreal Protocol on Substances that Deplete the Ozone Layer was developed calling for the progressive reduction in CFC use until their elimination.

The aerosol pharmaceutical products for the treatment of asthma and bronchopulmonary diseases are agreed to be essential and enjoy a temporary exemption. However it is believed that the medical use of CFCs will be discontinued in the near future. The ozone-destroying potential of CFCs is proportional to the chlorine content.

Hydrofluoroalkanes [(HFAs) known also as hydrofluorocarbons (HFCs)] contain no chlorine and are considered less destructive to ozone and these are proposed as substitutes for CFCs.

HFAs and in particular 1,1,1,2-tetrafluoroethane (HFA 134a) and 1,1,1,2,3,3,3-heptafluoropropane (HFA 227) have been acknowledged to be the best candidates for non-CFC propellants and a number of medicinal aerosol formulations using such HFA propellant systems are disclosed in several patent applications.

Many of these applications, in which HFAs are used as propellant, propose the addition of one or more of adjuvants including compounds acting as cosolvents, surface active agents including fluorinated and non-fluorinated surfactants, dispersing agents including alkylpolyethoxylates and stabilizers.

Cosolvents which may be used in these formulations include alcohols such as ethanol and polyols such as propylene glycol.

Medicinal aerosol formulations using such propellant systems are disclosed in, for example, EP 0372777. EP 0372777 requires the use of HFA 134a as a propellant in combination with both a surfactant and an adjuvant having higher polarity than the propellant.

For aerosol suspension compositions, a surfactant is often added to improve the physical stability of the suspension. EP 0372777 states that the presence of surfactant assists in the preparation of stable, homogeneous suspensions and may also assist in the preparation of stable solution formulations.

Surfactants also lubricate the valve components in the inhaler device.

The use of propylene glycol as a solvent having a higher polarity than the propellant in HFA pressurized metered dose inhalers formulations has been mentioned in several other patent applications and for example in:

EP 504112 relates to a pharmaceutical aerosol formulation free from CFCs containing a propellant (hydrocarbon, HFA or a mixture), one or more pharmaceutical active ingredients, a non-ionic surfactant and optionally other conventional pharmaceutical auxiliaries suitable for aerosol formulations comprising solvents having a higher polarity than the propellant, other non-ionic surfactants as valve lubricants, vegetable oils, phospholipids, taste masking agents.

DE 4123663 describes a medical aerosol composition containing a dispersion or suspension of an active agent in association with a compound with surface-active or lipophilic properties, heptafluoropropane as propellant and an alcohol such as ethanol and/or propylene glycol.

U.S. Pat. No. 5,534,242 describes an aerosol-dispensable pharmaceutical composition comprising lidocaine base and a vasoconstrictor dissolved in an HFA propellant and optionally an organic solvent.

Other applications propose the addition of dispersing agents to the composition. U.S. Pat. No. 5,502,076 concerns compositions used in inhalation aerosols comprising an HFA, leukotriene antagonists and dispersing agent comprising 3C-linked triesters, vitamin E acetate, glycerin, t-BuOH, or transesterified oil/polyethylene glycol.

EP 384371, describes a propellant for an aerosol, comprising pressure-liquefied HFA 227 in a mixture with pressure-liquefied propane and/or n-butane and/or iso-butane and/or dimethyl ether and/or 1,1-difluoroethane. The document also discloses foam formulations (shaving and shower foams) containing glycerol as additive.

The effectiveness of an aerosol device, for example an MDI, is a function of the dose deposited at the appropriate site in the lungs. Deposition is affected by several factors, of which one of the most important is the aerodynamic particle size. Solid particles and/or droplets in an aerosol formulation can be characterized by their mass median aerodynamic diameter (MMAD, the diameter around which the mass aerodynamic diameters are distributed equally).

Particle deposition in the lung depends largely upon three physical mechanisms: (1) impaction, a function of particle inertia; (2) sedimentation due to gravity; and (3) diffusion resulting from Brownian motion of fine, submicrometer (<1 µm) particles. The mass of the particles determines which of the three main mechanisms predominates.

The effective aerodynamic diameter is a function of the size, shape and density of the particles and will affect the magnitude of forces acting on them. For example, while inertial and gravitational effects increase with increasing particle size and particle density, the displacements produced by diffusion decrease. In practice, diffusion plays little part in deposition from pharmaceutical aerosols. Impaction and sedimentation can be assessed from a measurement of the mass median aerodynamic diameter (MMAD) which determines the displacement across streamlines under the influence of inertia and gravity, respectively.

Aerosol particles of equivalent MMAD and GSD (Geometric Standard Deviation) have similar deposition in the lung irrespective of their composition. The GSD is a measure of the variability of the aerodynamic particle diameters.

For inhalation therapy there is a preference for aerosols in which the particles for inhalation have a diameter of about 0.8 to 5 µm. Particles which are larger than 5 µm in diameter are primarily deposited by inertial impaction in the oropharynx, particles 0.5 to 5 µm in diameter, influenced mainly by gravity, are ideal for deposition in the conducting airways, and particles 0.5 to 3 µm in diameter are desirable for aerosol delivery to the lung periphery. Particles smaller than 0.5 µm may be exhaled.

Respirable particles are generally considered to be those with aerodynamic diameters less than 5 µm. These particles, particularly those with a diameter of about 3 µm, are efficiently deposited in the lower respiratory tract by sedimentation.

It has been recently demonstrated in patients with mild and severe airflow obstruction that the particle size of choice for a β2 agonist or anticholinergic aerosol should be approximately 3 µm (Zaanen P et al. Int J Pharm 1994, 107:211-7; Int J Pharm 1995, 114:111-5; Thorax 1996, 51:977-980).

Besides the therapeutic purposes, the size of aerosol particles is important in respect to the side effects of the drugs. For example, it is well known that the oropharynx deposition of aerosol formulations of steroids can result in side effects such as Candidaisis of mouth and throat.

On the other hand a higher systemic exposure to the aerosol particles due to deep lung penetration can enhance the undesired systemic effects of the drugs. For example, the systemic exposure to steroids can produce side effects on bone metabolism and growth.

It has been reported that the particle size characteristics of HFA aerosol formulations of the state of the art are often very different from the products to be replaced.

EP 0553298 describes an aerosol formulation comprising: a therapeutically effective amount of beclomethasone 17,21 dipropionate (BDP); a propellant comprising a hydrofluorocarbon selected from the group consisting of HFA 134a, HFA 227, and a mixture thereof, and ethanol in an amount effective to solubilize the beclomethasone 17,21 dipropionate in the propellant. The formulation is further characterized in that substantially all of the beclomethasone 17,21 dipropionate is dissolved in the formulation and that the formulation contains no more than 0.0005% by weight of any surfactant.

It has been reported in literature that these new formulations of beclomethasone dipropionate (BDP) as a solution in HFA 134a deliver a particle size distribution with a MMAD of 1.1 µm. This means that the peripheral pulmonary deposition of very small particles increases and submicronic particles can easily be directly absorbed from the alveoli into the bloodstream. The rate and extent of systemic absorption is significantly increased and as a consequence undesired effects for example certain side effects can increase. A relatively large fraction of the dose is exhaled. The implications of this for clinical efficacy and toxic effects are great. They arise because the principles of formulation using HFAs may modify the physical form of the respired cloud.

SUMMARY OF THE INVENTION

According to the invention there is provided a composition for use in an aerosol inhaler, the composition comprising an active material, a propellant containing a hydrofluoroalkane (HFA), a cosolvent and further comprising a low volatility component to increase the mass median aerodynamic diameter (MMAD) of the aerosol particles on actuation of the inhaler.

The nature and concentration of the low volatility component can be chosen to influence, for example, the size and/or the density of the particle, both of which affect the MMAD.

It is an object of the invention to provide an aerosol formulation which avoids or mitigates the problems indicated above and in particular provides an aerosol composition including HFA as propellant having similar size characteristics to the CFC compositions which they replace. That would help to provide an MDI having HFAs as propellant which was pharmaceutically and clinically equivalent to the MDIs which use CFCs.

DETAILED DESCRIPTION OF THE PREFERRED EMBODIMENTS

Although most commonly applied to formulae in which the active agent(s) is in solution, the principle can also be applied to suspension formulae and to mixed formulae in which only one of the components is present in solution form.

The invention thus allows the design of formulae using HFAs with similar particle size characteristics to those of the CFC formulations they replace. This allows development of products which are pharmaceutically and clinically equivalent to the CFC formulation.

Examples of low volatility components which may be included in the aerosol formulation to increase the MMAD of the aerosol particles include high density components, for example glycerol and propylene glycol, and low density compounds, for example oleic acid and certain vegetable oils.

Glycerol and propylene glycol have previously been investigated as additives in aqueous systems in relation to the nebulization of fluids by jet or ultrasonic nebulizers. The contents of propylene glycol or glycerol in these systems was very high (10-50% v/v). The results were equivocal.

Davis S S in Int J Pharm 1(2), 71-83, 1978 examined the aerosolization characteristics of two common nebulizers using a propylene glycol-water systems. The output of aerosol solution droplets passed through a max. at 30% vol./vol. propylene glycol; an increased output was parallelled by an increased particle size.

Davis S S et al. in Int J Pharm 1(2), 85-93, 1978 examined the output of aerosol droplets from a common nebulizer using a water-propylene glycol-ethanol system.

In general an increased alcohol content led to an increased total output from the nebulizer. However, much of this output was in the form of solvent vapour and only a modest increase in the output of therapeutically effective aerosol droplets was obtained.

Miller W C and Mason J W in J Aerosol Med 4(4), 293-4, 1991 used radioaerosol techniques to determine if adding propylene glycol would improve aerosol delivery of a jet nebulizer in spontaneously breathing normal human subjects. They found no significant differences in either deposition or penetration between saline control and a 20% propylene glycol solution.

McCallion et al. in Pharm Res 12(11), 1682-7, 1995 sought to evaluate in three types of jet nebulizer and two ultrasonic devices the influence on the aerosol's size and output characteristics of fluid systems containing water, ethanol, glycerol 10-50% (v/v) solutions, propylene glycol 10-50% (v/v) solutions and silicone fluids 200/0.65 cs-200/100 cs. The parameters considered were viscosity and surface tension.

Oleic acid has been used in aerosol formulations, in order to improve the physical stability of drug suspensions, as a dispersing agent useful in keeping the suspended particles from agglomerating.

It has now been surprisingly found that in solution formulations of the present application oleic acid can be used either as solubilizer and/or stabilizer of the active ingredient or a low volatility component.

When used as solubilizer/stabilizer the amount of oleic acid can be varied according to the concentration and the characteristics of the active material. When used as low volatility component the percentage concentration of oleic acid should be preferably no less than 0.5% w/w.

In general terms the low volatility component can be any compound, safe and compatible with the propellant system of the invention capable to influence either the size or the density of the aerosol particle so affecting the MMAD.

As it can be noticed from the results reported in the tables, the influence of the low volatility component on the MMAD of the particles is correlated to its density. The higher the density of the low volatile ingredient, the higher the increase of the MMAD of the aerosol particles on actuation of the inhaler.

The applications concerning aerosol formulations using the new propellant systems disclosed in the known prior art seek to overcome problems of stability of the formulations. The present application seeks a solution both for the stability of the formulations and to the therapeutic problems associated with the new medicinal aerosols, as the presence in the formulation of a low volatility ingredient influences the most important factor affecting aerosol delivery to the Lung: the aerodynamic mass of the particles.

It has surprisingly been found that by adding a low volatility component to the composition, the MMAD of the aerosol particles on actuation of the inhaler can be increased and thus the compositions may be formulated so that the aerodynamic particle size characteristics are similar to those for the CFC-propellant compositions.

Advantageously, the low volatility component has a vapour pressure at 25° C. not more than 0.1 kPa, preferably not more than 0.05 kPa. We have found that with the addition of components having such low vapour pressures, control of the MMAD may be obtained.

It is thought that the addition of the component having a low vapour pressure depresses the atomisable characteristics of the HFA propellant giving larger particles on actuation of the inhaler and after evaporation of the propellant.

The low vapour pressure of the low volatility component is to be contrasted with that of the cosolvent which preferably has a vapour pressure at 25° C. not less than 3 kPa, more preferably not less than 5 kPa.

The cosolvent has advantageously a higher polarity than that of the propellant and the cosolvent is used to increase the solubility of the active material in the propellant.

Advantageously the cosolvent is an alcohol. The cosolvent is preferably ethanol. The cosolvent may include one or more materials.

The low volatility component may be a single material or a mixture of two or more materials.

We have found that glycols are particularly suitable for use as the low volatility component, especially propylene glycol, polyethylene glycol and glycerol.

Other particularly suitable materials are thought to include other alcohols and glycols, for example alkanols such as decanol (decyl alcohol), sugar alcohols including sorbitol, mannitol, lactitol and maltitol, glycofural (tetrahydro-furfurylalcohol) and dipropylene glycol.

It is also envisaged that various other materials may be suitable for use as the low volatility component including vegetable oils, organic acids for example saturated carboxylic acids including lauric acid, myristic acid and stearic acid; unsaturated carboxylic acids including sorbic acid, and especially oleic acid; saccharine, ascorbic acid, cyclamic acid, amino acids, or aspartame might be used.

The low volatility component may include esters for example ascorbyl palmitate and tocopherol; alkanes for example dodecane and octadecane; terpenes for example menthol, eucalyptol, limonene; sugars for example lactose, glucose, sucrose; polysaccharides for example ethyl cellulose, dextran; antioxidants for example butylated hydroxytoluene, butylated hydroxyanisole; polymeric materials for example polyvinyl alcohol, polyvinyl acetate, polyvinyl pyrollidone; amines for example ethanolamine, diethanolamine, triethanolamine; steroids for example cholesterol, cholesterol esters.

The amount of low volatility component in the composition depends to some extent upon its density and the amount of active material and cosolvent in the composition. Advantageously, the composition includes not more than 20% by weight of the low volatility component. Preferably the composition includes not more than 10% by weight of the low volatility component.

On actuation of the inhaler, the propellant and the ethanol vaporise but because of the low vapour pressure of the low volatility component, that component generally will not.

It is thought that it is preferable for the composition to contain at least 0.2%, preferably at least 1% by weight of the low volatility component. The composition may contain between 1% and 2% by weight.

Most advantageously, the composition is such that, on actuation of the aerosol inhaler in use, the MMAD of the aerosol particles is not less than 2 µm. For some active materials the MMAD is preferably not less than 2.5 µm and for a few formulations, the preferred MMAD will be greater than 3 µm or even greater than 4 µm. As is indicated in the examples below, for one corresponding inhaler formulation using CFC propellants, the MMAD of the aerosol particles is approximately 2.8 µm (see Table 4 below).

Preferred HFA propellants are HFA 134a and HFA 227. The propellant may comprise a mixture of more than one component.

The composition may be in the form of a solution or a suspension or an ultrafine suspension or colloidal solution. The invention is particularly relevant where the composition is a solution but also relates to suspension, in particular those of small particle size. Preferably the composition is a solution.

In some cases a small quantity of water may be added to the composition to improve the solution of the active material and/or the low volatility component in the cosolvent.

The active material may be one or more of any biologically active material which could be administered by inhalation. Active materials commonly administered in that way include β2 agonists, for example salbutamol and its salts, steroids for example beclomethasone dipropionate or anti-cholergics for example ipratropium bromide.

The invention further provides use of a low volatility component in a composition for an aerosol inhaler, the composition comprising an active material, a propellant containing a hydrofluoroalkane (HFA) and a cosolvent, to increase the mass median aerodynamic diameter (MMAD) of the aerosol particles on actuation of the inhaler.

As indicated above, on actuation of the inhaler, the aerosol particles advantageously have an MMAD of not less than 2 μm, for many formulations more preferably not less than 2.5 μm.

As described above, the low volatility component advantageously has a vapour pressure at 25° C. not more than 0.1 kPa.

The invention also provides an inhaler containing the composition in accordance with the invention.

Also provided is a method of filling an aerosol inhaler with a composition, the method comprising filling the following components into the inhaler
(a) one or more active materials,
(b) one or more low volatility components,
(c) one or more cosolvents followed by the addition of a propellant containing a hydrofluoroalkane (HFA).

The invention further provides aerosol particles emitted from an aerosol inhaler containing a composition, the composition comprising an active component, a propellant containing a hydrofluoroalkane (HFA.), a cosolvent and a low volatility component, wherein the mass median aerodynamic diameter (MMAD) of the aerosol particles is not less than 2 μm.

For some compositions, it is preferred that the MMAD of the particles is not less than 2.5 μm as indicated above.

The particles will usually be in the form of droplets.

Embodiments of the invention will now be described by way of example.

The aerosol compositions of the invention described below were prepared by the following method. The required components of a composition were added into a can in the following order: drug, non-volatile additive, absolute ethanol. After crimping of the valve on to the can, the propellant was added through the valve. The weight gain of the can after each component was added was recorded to allow the percentage, by weight, of each component in the formulation to be calculated.

The aerodynamic particle size distribution of each formulation was characterized using a Multistage Cascade Impactor according to the procedure described in the European Pharmacopoeia 2nd edition, 1995, part V.5.9.1. pages 15-17. In this specific case an Andersen Cascade Impactor (ACI) was used. Results represented were obtained from ten cumulative actuations or a formulation. Deposition of the drug on each ACI plate was determined by high pressure liquid chromatography. The mass median aerodynamic diameter (MMAD) and geometric standard deviation (GSD) were calculated from plots of the cumulative percentage undersize of drug collected on each ACI plate (probit scale), against the upper cut off diameter for each respective ACI plate (log10 scale). The fine particle dose of each formulation was determined from the mass of drug collected on Stages 2 through to Filter (<5.8 μm) divided by the number of actuations per experiment.

Tables 1 and 2 show comparative examples indicating the characteristics of aerosol formulations containing HFA 134a, different beclomethasone dipropionate (BDP) (active material) amounts and different ethanol concentrations. The formulations do not contain a low volatility component. As can be seen, the MMAD is not substantially influenced by the ratio of cosolvent to propellant.

Increase of the concentration of the active ingredient gives a slight variation of MMAD which, in this case, is correlated with the BDP content.

For equal concentrations of BDP the content of ethanol and the addition up to 0.5% of water does not significantly affect the MMAD.

Table 3 compares the characteristics of a CFC ipratropium bromide (IPBr) standard formulation with HFA 134a, ethanol, ipratropium bromide solution formulations with a content of glycerol from 0 to 1%.

It can be seen that the MMAD of the formulation having the HFA as propellant is significantly lower than that for the conventional CFC formulation.

The MMAD of the HFA/ethanol-IPBr formulations is 1.2±1.9 or 1.3±0.1 μm depending on the content of ethanol (respectively 12.9±0.1% w/w and 25% w/w), in comparison with an MMAD of 2.8±0.1 μm of the CFC-IPBr formulation.

The addition of a low volatile additive such as glycerol increases the particle MMAD of the HFA solution formulations; the increase is correlated with the glycerol concentration.

In confirmation of the results of Tables 1 and 2 the MMAD is not substantially influenced by the ratio of cosolvent to propellant.

In other studies the effects of increasing concentrations of propylene glycol, glycerol and polyethylene glycol (PEG) in HFA 134a and ethanol beclomethasone dipropionate (BDP) formulations have been determined.

The % indicated for the components of the composition are % by weight unless indicated to the contrary.

The results are reported in Tables 4, 5, 6, 7 and 8.

The results show the direct relationship between the percentage of low volatile ingredient and particle MMAD. As we can notice there is a slight influence of the actuator orifice on the MMAD but the relationship between the concentration of low volatile ingredient and particle MMAD is maintained. These findings demonstrate that the addition of an established amount of low volatile additives in HFA formulations can increase the MMAD of the particles to values comparable to the MMAD of the previously known CFC formulations which the HFA formulations seek to replace.

Advantageously, the GSD is not significantly changed on addition of the low volatility component. In particular, for glycerol as the low volatility component, Tables 6 and 7 show that the GSD is not substantially changed by the addition of glycerol. Glycerol is a particularly preferred material for the low volatility component.

The increase in particle MMAD by the addition of an established amount of glycerol in HFA solution formulation has been observed also with flunisolide (Table 9), in the presence of a moderate concentration of a taste corrective such as menthol.

Analogous results have been obtained with salbutamol, as it can be noticed in Table 10. A small amount of oleic acid (0.3%) has been added to the formulation to improve the physical stability of the solution. In this concentration the oleic acid does not substantially modify the particle MMAD of the active material.

In Table 11 HFA 134a, ethanol 15.4±0.2%, BDP in combination with salbutamol formulations without and in presence of 1.2% of glycerol and with a content of oleic acid from 0 to 1.3% are compared.

The results show that:

a) the MMAD of the two active materials in solution combination without low volatility components is practically the same as the single compounds;
b) oleic acid in concentration of 1.3% acts as low density low volatile compound and produces an appreciable increase in particle MMAD;
c) the influence of the low volatility component of the MMAD is correlated to its density; oleic acid in concentration of 1.3% produces an increase in MMAD to a definitely less extent than 1.2% of glycerol, which has a higher density;
d) the presence in the formulation of two active materials, the low volatility ingredient and the stabilizer, does not cause any interference between the components.

Oleic acid is another preferred material for a low density low volatility component.

Finally, Table 12 shows that the addition of a low volatility component allows the modulation of the MMAD of an active material formulated as a solution in an HFA 227/ethanol system.

Therefore, the formulations of the invention allow improvement of the delivery characteristics of drugs to the lung by modulating the aerodynamic particle size and size distribution so that the pattern of deposition gives an equivalent clinical effect.

The entire disclosure of application Ser. No. 09/796,607, of which the subject application is a continuation, is incorporated by reference.

TABLE 1

BDP formulations in HFA 134a
and ethanol—Actuator orifice 0.25 mm

|  | BDP 10 mg/ 10 ml ethanol 7.9% | BDP 10 mg/ 10 ml ethanol 12.9-13.0% | BDP 20 mg/ 10 ml ethanol 7.9% | BDP 20 mg/ 10 ml ethanol 13.0% |
|---|---|---|---|---|
| Mean emitted dose (µg) | 44.7 | 45.1 | 84.8 | 87.6 |
| Fine particle dose (µg) | 31.1 | 24.5 | 63.1 | 46.2 |
| MMAD ± GSD | 0.8 ± 1.8 | 0.9 ± 2.0 | 1.0 ± 1.8 | 1.0 ± 1.9 |
| Shot weight (mg) | 59.0 | 58.7 | 59.1 | 57.6 |
| Replications | 6 | 2 | 6 | 2 |

TABLE 2

BDP formulations in HFA 134a, ethanol and
small amounts of water (up to 0.5%)—Actuator orifice 0.33 mm

|  | BDP 10 mg/ 10 ml ethanol 13.7% $H_2O$ 0.1% | BDP 10 mg/ 10 ml ethanol 13.6% $H_2O$ 0.5% | BDP 50 mg/ 10 ml ethanol 14.9% $H_2O$ 0.1% | BDP 50 mg/ 10 ml ethanol 14.9% $H_2O$ 0.5% |
|---|---|---|---|---|
| Mean emitted dose (µg) | 43.2 | 42.9 | 222.1 | 215.1 |
| Fine particle dose (µg) | 14.9 | 12.7 | 67.4 | 60.2 |
| MMAD (µm) ± GSD | 1.0 ± 2.2 | 1.0 ± 2.1 | 1.8 ± 2.2 | 1.7 ± 2.2 |
| Shot weight (mg) | 58.1 | 58.0 | 59.0 | 57.5 |
| Replications | 6 | 6 | 6 | 6 |

TABLE 3

Comparison of standard CFC ipratropium bromide formulation
(4 mg/10 ml IPBr) and HFA 134a/ethanol-ipratropium bromide
solution without and in presence of increasing amount of glycerol

| Formulations | CFC-IPBr | HFA 134a/ ethanol 25% - IPBr ** | HFA 134a-IPBr * | | |
|---|---|---|---|---|---|
| Glycerol content (%) |  | 0 | 0 | 0.5 | 1.0 |
| Mean emitted dose (µg) | 18.8 | 17.1 | 16.1 | 18.7 | 18.8 |
| Fine particle dose (µg) | 6.1 | 2.6 | 3.9 | 6.9 | 5.6 |
| MMAD (µm) ± GSD | 2.8 ± 1.8 | 1.3 ± 2.0 | 1.2 ± 1.9 | 1.9 ± 2.0 | 2.5 ± 2.1 |
| Shot weight (mg) | 75.4 | 55.7 | 58.0 | 59.0 | 58.3 |
| Replications | 3 | 4 | 6 | 6 | 6 |

* HFA formulation: 4 mg/10 ml IPBr; ethanol 12.9 ± 0.1% (w/w); HFA 134a fill to 12 ml.
** IPBr 4 mg/10 ml; HFA 134a fill to 12 ml
Actuator orifice: 0.33 mm

TABLE 4

Comparison of BDP formulations in HFA 134a and ethanol in the
presence of increasing amount of propylene glycol

|  | Propylene glycol content | | | |
|---|---|---|---|---|
|  | 0.0% (w/w) | 1.1% (w/w) | 3.2% (w/w) | 6.8% (w/w) |
| Mean emitted dose (µg) | 41.8 | 44.0 | 43.6 | 44.9 |
| Fine particle dose (µg) | 10.3 | 9.3 | 7.3 | 4.9 |
| MMAD (µm) ± GSD | 1.1 ± 2.3 | 1.6 ± 3.4 | 2.9 ± 4.1 | 4.6 ± 3.9 |
| Replications | 2 | 6 | 6 | 6 |

Formulation: BDP 10 mg/10 ml; ethanol 12.9 ± 0.1% (w/w); HFA 134a fill to 12 ml.
Actuator orifice: 0.42 mm

TABLE 5

Comparison of BDP formulations in HFA 134a and ethanol in the presence of increasing amount of propylene glycol

| | Propylene glycol content | | | |
|---|---|---|---|---|
| | 0.0% (w/w) | 0.7% (w/w) | 2.8% (w/w) | 6.3% (w/w) |
| Mean emitted dose (µg) | 209.1 | 218.4 | 204.2 | 242.6 |
| Fine particle dose (µg) | 41.6 | 41.1 | 32.1 | 25.2 |
| MMAD (µm) ± GSD | 1.7 ± 2.3 | 2.1 ± 2.7 | 3.3 ± 3.2 | 4.4 ± 3.8 |
| Replications | 3 | 3 | 3 | 3 |

Formulation: BDP 50 mg/10 ml; ethanol 15.2 ± 0.4% (w/w); HFA 134a fill to 12 ml.
Actuator orifice: 0.42 mm

TABLE 6

Comparison of BDP formulations in HFA 134a and ethanol in the presence of increasing amount of glycerol

| | Glycerol content | | | |
|---|---|---|---|---|
| | 0.0% (w/w) | 1.0% (w/w) | 1.3% (w/w) | 1.6% (w/w) |
| Mean emitted dose (µg) | 205.8 | 218.3 | 220.8 | 228.0 |
| Fine particle dose (µg) | 105.9 | 94.4 | 100.3 | 96.6 |
| MMAD (µm) ± GSD | 1.4 ± 1.9 | 2.4 ± 2.0 | 2.6 ± 2.0 | 2.7 ± 2.0 |
| Replications | 6 | 3 | 3 | 2 |

Formulation: BDP 50 mg/10 ml; ethanol 15.0 ± 0.2% (w/w); HFA 134a fill to 12 ml
Actuator orifice: 0.25 mm

TABLE 7

Comparison of BDP formulations in HFA 134a and ethanol in the presence of increasing amount of glycerol

| | Glycerol content | | | |
|---|---|---|---|---|
| | 0.0% (w/w) | 1.0% (w/w) | 1.3% (w/w) | 1.6% (w/w) |
| Mean emitted dose (µg) | 222.1 | 227.9 | 228.4 | 231.7 |
| Fine particle dose (µg) | 67.4 | 55.9 | 54.3 | 50.9 |
| MMAD (µm) ± GSD | 1.8 ± 2.2 | 2.8 ± 2.2 | 3.1 ± 2.3 | 3.1 ± 2.3 |
| Replications | 6 | 4 | 3 | 2 |

Formulation: BDP 50 mg/10 ml; ethanol 15.0 ± 0.2% (w/w); HFA 134a fill to 12 ml
Actuator orifice: 0.33 mm

TABLE 8

Comparison of BDP formulations in HFA 134a and ethanol in the presence of polyethylene glycol (PEG) 400 or 8000

| | PEG 400 1.1% (w/w) | PEG 8000 1.0% (w/w) | 0.0% (w/w) |
|---|---|---|---|
| Mean emitted dose (µg) | 218.9 | 215.0 | 222.1 |
| Fine particle dose (µg) | 55.6 | 55.6 | 67.4 |
| MMAD (µm) ± GSD | 2.5 ± 2.2 | 2.5 ± 2.2 | 1.8 ± 2.2 |
| Replications | 2 | 1 | 6 |

Formulation: BDP 50 mg/10 ml; ethanol 14.9 ± 0.1% (w/w); HFA 134a fill to 12 ml
Actuator orifice: 0.33 mm

TABLE 9

Comparison of Flunisolide solution formulations in HFA 134a and ethanol without and in presence of glycerol

| Menthol % (w/w) | Glycerol % (w/w) | Fine Particle Dose (FPD) (µg) | MMAD | GSD | Emitted Dose (µg) | Replications (n) |
|---|---|---|---|---|---|---|
| 0 | 0 | 76.85 | 1.8 | 2.15 | 217.1 | 2 |
| 0.4 | 0.9 | 77.84 | 2.9 | 2.1 | 221.6 | 5 |

Formulation: Flunisolide 50 mg/10 ml; ethanol 15.0 ± 0.1%; HFA 134a fill to 12 ml
Actuator orifice: 0.30 mm

TABLE 10

Comparison of Salbutamol base solution formulations in HFA 134a and ethanol without and in presence of glycerol

| Glycerol % (w/w) | Oleic Acid % (w/w) | Emitted dose (µg) | FPD (µg) | MMAD (µm) | GSD | Replications (n) |
|---|---|---|---|---|---|---|
| 0 | 0.35 | 85.8 | 29.1 | 1.7 | 2.3 | 1 |
| 1.3 | 0.36 | 92.0 | 25.2 | 2.8 | 2.4 | 1 |

Formulation: Salbutamol base 20 mg/10 ml; ethanol 15% (w/w); HFA 134a fill to 12 ml
Actuator orifice: 0.30 mm

TABLE 11

BDP and Salbutamol base combination in solution formulations in HFA 134a and ethanol, without and in presence of glycerol, oleic acid and their combination

| Glycerol % (w/w) | Oleic Acid % (w/w) | BDP Emitted dose (µg) | BDP FPD (µg) | BDP MMAD (µm) | BDP GSD | Salbutamol Base Emitted dose (µg) | Salbutamol Base FPD (µg) | Salbutamol Base MMAD (µm) | Salbutamol Base GSD | Actuator exit orifice (mm) | n |
|---|---|---|---|---|---|---|---|---|---|---|---|
| 0 | 0 | 208.9 | 67.8 | 1.7 | 2.4 | 82.5 | 26.9 | 1.7 | 2.2 | 0.33 | 2 |
| 0 | 0.3 | 212.7 | 60.6 | 2.2 | 2.3 | 84.8 | 24.0 | 2.0 | 2.6 | 0.33 | 2 |

TABLE 11-continued

BDP and Salbutamol base combination in solution formulations in HFA 134a and ethanol, without and in presence of glycerol, oleic acid and their combination

| Glycerol % (w/w) | Oleic Acid % (w/w) | BDP | | | | Salbutamol Base | | | | Actuator exit orifice (mm) | n |
|---|---|---|---|---|---|---|---|---|---|---|---|
| | | Emitted dose (µg) | FPD (µg) | MMAD (µm) | GSD | Emitted dose (µg) | FPD (µg) | MMAD (µm) | GSD | | |
| 0 | 1.3 | 212.5 | 58.5 | 2.4 | 2.2 | 85.9 | 23.9 | 2.4 | 2.1 | 0.30 | 1 |
| 1.2 | 0.3 | 210.8 | 63.3 | 2.9 | 2.1 | 85.3 | 25.1 | 3.0 | 2.0 | 0.30 | 1 |

Formulation: BDP 50 mg/10 ml; Salbutamol base 20 mg/10 ml; ethanol 15.4 ± 0.2% (w/w); HFA 134a fill to 12 ml

TABLE 12

BDP 50 mg/10 ml formulations in HFA 227 and ethanol 15.0 ± 0.2% (w/w), with and without glycerol as a non volatile additive. HFA 227 fill to 12 ml; Actuator orifice 0.33 mm

| | HFA 227 | |
|---|---|---|
| | 0% (w/w) Glycerol | 1.42% (w/w) Glycerol |
| FPD (µg) | 62.1 | 43.5 |
| MMAD (µm) | 2.2 | 4.1 |
| GSD | 2.6 | 2.4 |
| Mean emitted dose (µg) | 221.25 | 230.5 |
| Replications | 2 | 2 |

The invention claimed is:

1. A composition, which is a formulation for an aerosol inhaler in the form of a solution of a therapeutically active medicament, said composition consisting of:
    (a) one or more therapeutically active medicaments,
    (b) glycerol in an amount of 0.2 to 2% of said composition,
    (c) ethanol as a co-solvent, and
    (d) a propellant consisting of at least one hydrofluoroalkane selected from the group consisting of 1,1,1,2-tetrafluoroethane, 1,1,1,2,3,3,3-heptafluoropropane, and a mixture thereof.

2. A composition as defined in claim 1, wherein said propellant is 1,1,1,2-tetrafluoroethane.

3. A composition according to claim 1, wherein said active medicament is beclomethasone dipropionate.

4. A composition as defined in claim 1, wherein said active medicament is selected from the group consisting of beclomethasone diproprionate, ipratropium bromide, flunisolide and salbutamol and its salts.

5. A composition as defined in claim 1, wherein the mass median aerodynamic diameter of the aerosol particles emitted upon activation of an inhaler which contains said composition is from 2 µm to 4.1 µm.

6. A composition according to claim 1, wherein said glycerol is present in said composition in an amount of 0.2 to 1.6% of said composition.

7. A composition according to claim 1, wherein said glycerol is present in said composition in an amount between 1% and 2% of said composition.

8. A composition according to claim 1, wherein said glycerol is present in said composition in an amount of 1 to 1.6% of said composition.

* * * * *